United States Patent [19]

Okushima et al.

[11] 4,323,500
[45] Apr. 6, 1982

[54] METHOD FOR PREPARING 7α-ACYLTHIO-4-EN-3-OXOSTEROIDS

[75] Inventors: Hiromi Okushima, Kawasaki; Shinichiro Fujimori, Yokohama; Rikizo Furuya, Yokohama; Shuzo Hayakawa, Yokohama, all of Japan

[73] Assignee: Mitsubishi Chemical Industries, Limited, Tokyo, Japan

[21] Appl. No.: 240,949

[22] Filed: Mar. 5, 1981

[30] Foreign Application Priority Data

Mar. 13, 1980 [JP] Japan .................................. 55-31789

[51] Int. Cl.³ .............................................. C07J 17/00
[52] U.S. Cl. .............................................. 260/239.57
[58] Field of Search .................................. 260/239.57

[56] References Cited

U.S. PATENT DOCUMENTS 3,883,512  5/1975  Stache et al. ...................... 424/241
4,211,701  7/1980  Temko ............................ 260/239.57
4,265,816  5/1981  Okushima et al. ............... 260/239.57

*Primary Examiner*—Elbert L. Roberts
*Attorney, Agent, or Firm*—Oblon, Fisher, Spivak, McClelland & Maier

[57] ABSTRACT

A 7α-acylthio-4-en-3-oxosteroid such as 7α-acetylthio-17-hydroxy-3-oxo-17α-pregn-4-ene-21-carboxylic acid γ-lactone (spironolactone) which is an antialdosteronic diuretic effective in therapy is prepared by contacting a steroidal material which contains a 7β-acylthio-4-en-3-oxosteroid with a thiocarboxylic acid.

12 Claims, No Drawings

METHOD FOR PREPARING 7α-ACYLTHIO-4-EN-3-OXOSTEROIDS

BACKGROUND OF THE INVENTION

1. Field of the Invention

This invention relates to a method for preparing 7α-acylthio-4-en-3-oxosteroids. More particularly, it relates to a commercial method for preparing a 7α-acylthio-4-en-3-oxosteroid (hereinafter referred to as "7α-acylthio derivative") such as 7α-acetylthio-17-hydroxy-3-oxo-17α-pregn-4-ene-21-carboxylic acid γ-lactone (hereinafter referred to as "spironolactone") which is an antialdosteronic diuretic extremely effective in therapy.

In one embodiment, this invention relates to a method for converting 7β-acetylthio-17-hydroxy-3-oxo-17α-pregn-4-ene-21-carboxylic acid γ-lactone (hereinafter referred to as "7β-acetylthio derivative") which is therapeutically inactive into the spironolactone, that is, its 7α-acetylthio derivative, extremely effective in therapy in a high yield.

2. Description of the Prior Art

It is known that spironolactone is usually prepared by reacting 17-hydroxy-3-oxo-17α-pregna-4,6-diene-21-carboxylic acid γ-lactone with a large excess of thioacetic acid under heating [J. Org. Chem., 27, 3325(1962)]. According to such method, however, the 7β-acetylthio derivative which is therapeutically inactive is formed as a by-product in a proportion of about 25%.

Accordingly, in order to obtain spironolactone from 17-hydroxy-3-oxo-17α-pregna-4,6-diene-21-carboxylic acid γ-lactone in a high yield it is necessary to convert the undesirable 7β-acetylthio derivative into the spironolactone by some means.

In a conventional procedure, the reaction mixture of the above-mentioned addition reaction is worked up by a suitable purification technique such as crystallization to isolate the spironolactone of high purity. As a result, the filtrate or mother liquor contains a relatively large amount of spironolactone together with the 7β-acetylthio derivative by-product.

The 7β-acetylthio derivative can be converted into the spironolactone by treating the 7β-acetylthio derivative with a base such as sodium hydroxide or sodium methoxide to give the starting material, 17-hydroxy-3-oxo-17α-pregna-4,6-diene-21-carboxylic acid γ-lactone, followed by the addition reaction with thioacetic acid. (This method is hereinafter referred to as "elimination-addition method".)

However, it has been found in our experiments that the elimination-addition method suffers from several disadvantages. First, the intermediate 17-hydroxy-3-oxo-17α-pregna-4,6-diene-21-carboxylic acid γ-lactone cannot be obtained in an yield exceeding 90% and appreciable amounts of by-products are formed. Accordingly, the 17-hydroxy-3-oxo-17α-pregna-4,6-diene-21-carboxylic acid γ-lactone obtained in this way does not have enough purity to use it as the starting material for the thioacetic acid addition reaction which is intended to provide the spironolactone of high purity, and usually it must be purified prior to use, which results in a further decrease in the actual yield.

Secondly, the method is disadvantageous in that the relatively large amount of spironolactone usually accompanying the crude 7β-acetylthioderivative is also returned to the starting material, 17-hydroxy-3-oxo-17α-pregna-4,6-diene-21-carboxylic acid γ-lactone during the base treatment involved in the method.

Thirdly, since both the 7β-acetylthio derivative and spironolactone are returned to the starting material, 17-hydroxy-3-oxo-17α-pregna-4,6-diene-21-carboxylic acid γ-lactone, the addition reaction of thioacetic acid must be conducted again to give the desired spironolactone. During such reaction, as previously mentioned, the therapeutically inactive 7β-acetylthio derivative is formed again as by-product and hence the overall yield of the spironolactone is relatively low.

Finally, it is evident from the above that the elimination addition method is highly disadvantageous as a commercial method since it requires a large number of steps and complicated procedures.

SUMMARY OF THE INVENTION

It has now been found that a 7β-acylthio-4-en-3-oxosteroid (hereinafter referred to as "7β-acylthio derivative") can be converted into its 7α-acylthio derivative in a high yield with an entirely simple procedure, that is, by contacting the 7β-acylthio derivative with a thiocarboxylic acid.

Thus, the present invention provides a method for preparing a 7α-acylthio derivative which comprises contacting a steroidal material containing the corresponding 7β-acylthio derivative with a thiocarboxylic acid.

DETAILED DESCRIPTION OF THE PREFERRED EMBODIMENTS

In accordance with the invention, the steroidal material used as the starting material contains a 7β-acylthio derivative. Examples of the 7β-acylthio derivative include 7β-acetylthio-17-hydroxy-3-oxo-17α-pregn-4-ene-21-carboxylic acid γ-lactone, 7β-acetylthioandrost-4-ene-3,17-dione, 7β-acetylthio-17β-acetoxyandrost-4-en-3-one, 7β-acetylthio-1α,2α-methylene-17β-acetoxyandrost-4-en-3-one, 7β-acetylthio-17α-methyl, 17βacetoxyandrost-4-en-3-one, etc.

The starting steroidal material may contain, in addition to the 7β-acylthio derivative, one or more steroids such as 4,6-diene-3-oxosteroids, e.g., 17-hydroxy-3oxo-17α-pregna-4,6-diene-21-carboxylic acid γ-lactone, and 7α-acylthio derivatives, e.g., spironolactone.

This is generally the case, since, as previously mentioned, the 7β-acylthio derivatives usually exist as by-products and in unpurified conditions.

The 7β-acylthio derivative-containing steroidal material used as the starting material is usually obtained as a by-product, for example, from a 7α-acylthio derivative-producing process which involves the addition of a thiocarboxylic acid such as thioacetic acid or thiopropionic acid to a 4,6-diene-3-oxosteroid in a solvent.

Examples of the 4,6-diene-3-oxosteroid useful in such process include 17-hydroxy-3-oxo-17α-pregna-4,6-diene-21-carboxylic acid γ-lactone, androsta-4,6-diene-3,17-dione, 17β-acetoxy-androsta-4,6-diene-3-one, 1α,2α-methylene-17β-acetoxyandrosta-4,6-diene-3-one, 17α-methyl-17β-acetoxyandrosta-4,6-diene-3-one, etc.

N-methyl-2-pyrrolidone and N,N-dimethylacetamide are suitable for use as the solvent in the above process.

The above-mentioned process is advantageous in that not only the therapeutically active 7α-acylthio derivative is obtained in high yield, but the formation of by-products other than the desired 7-acylthio derivatives can be suppressed almost completely.

The solvent is used in an amount of 1 to 10 milliliter, preferably 3 to 6 milliliter per gram of the starting 4,6-dien-3-oxosteriod, while the thiocarboxylic acid is used in an amount of 1.1 to 20 moles, preferably 1.5 to 7 moles per mole of the starting steroid. The temperature at which the addition reaction is carried out ranges from 10 to 120° C., preferably from 30 to 100° C., more preferably 50 to 85° C. If desired, the addition reaction may be conducted in the presence of a catalytic amount of another acid which is stronger than the thiocarboxylic acid.

The product recovered from the addition reaction is a mixture of the 7α- and 7β-acylthio derivatives. The therapeutically active 7α-acylthio derivative can readily be separated for purification from the mixture in a conventional manner, for example, by means of crystallization.

When the 7α-acylthio derivative is purified by crystallization, an appropriate amount of water or a combination of water and a polar solvent is usually added to the reaction mixture and the resulting mixture is cooled and then filtered to isolate the precipitated 7α-acylthio derivative.

The remaining mother liquor (filtrate) from which the 7α-acylthio derivative has been separated generally contains the 7β-acylthio derivative, 7α-acylthio derivative and the unreacted 4,6-diene-3-oxosteroid. In the practice of the invention, the remaining solution is concentrated or alternatively an additional crop of crystals which contain the 7β-acylthio derivative are recovered from the solution by any suitable means such as crystallization, and the concentrate or crystals thus obtained can be used as the starting material to be contacted with a thiocarboxylic acid to give the desired 7α-acylthio derivative.

The thiocarboxylic acids used in the present invention include thioacetic acid, thiopropionic acid, thiobenzoic acid and the like. If none of the solvents described below is used, the thiocarboxylic acid is preferably used in an excess amount.

The method of the invention may be carried out in a solvent which is selected from those organic solvents which dissolve the starting steroid and in which the formed 7α-acylthio derivative is stable. Examples of such solvent include aromatic hydrocarbons such as benzene, toluene, xylene, etc.; alcohols such as methanol, ethanol, ethyl cellosolve, etc.; esters such as ethyl acetate, etc.; ethers such as tetrahydrofuran, ethylene glycol dimethyl ether, etc.; nitrogen-containing compounds such as N-methyl-2-pyrrolidone, N,N-dimethylacetamide, dimethylformamide, pyridine, etc.; and the like. Particularly preferable solvents are N-methyl-2-pyrrolidone and N,N-dimethylacetamide, because in these solvents the conversion of the 7β-acylthio derivative into the 7α-acylthio derivative is high, the formation of by-products is minimized and the desired 7α-acylthio derivative. is entirely stable.

The amount of thiocarboxylic acid used is usually 1.1 to 20 moles, preferably 1.5 to 7 moles per mole of the 7β-acylthio derivative present in the starting steroid. If the starting steroidal material contains a 7α-acylthio derivative and/or a 4,6-diene-3-oxosteroid, it is preferred to increase the amount of the thiocarboxylic acid by 1.5 to 7 moles per mole of the sum of these steroids.

The amount of the solvent used is in the range of 1 to 10 milliliter, preferably 3 to 6 milliliter per gram of the starting steroid.

The presence of a catalytic amount of an acid whose acidity is stronger than the thiocarboxylic acid is effective in the above-mentioned reaction in order to increase the rate of conversion of the starting material. Particularly suitable for this purpose is p-toluenesulfonic acid.

The reaction temperature may be between 10° and 120° C., preferably between 30° and 100° C. and more preferably between 50° and 85° C.

In accordance with the method of the present invention hereinbefore set forth, the ratio of the 7β-acylthio to 7α-acylthio derivative in the system reaches approximately 4 : 96 at the end of the reaction, with no or little formation of by-products other than the desired 7αacylthio derivative from the 7β-acylthio derivative. In addition, the formed 7αacylthio derivative is remarkably stable.

Having generally described this invention, a more complete understanding can be obtained by reference to certain examples which are provided herein for purposes of illustration only and are not intended to be limiting in any manner.

EXAMPLE 1

A mixture of 5.00 g of 17-hydroxy-3-oxo-17α-pregna-4,6-diene- 21-carboxylic acid γ-lactone (99.5% purity, 14.6 mmole), 15 ml of N-methyl-2-pyrrolidone and 228 mg of p-toluene-sulfonic acid monohydrate was heated to 80° C. in a nitrogen atmosphere. Then 3.0 ml of thioacetic acid was added and the mixture was stirred for 2 hours. At a temperature of 80° C., 5 ml of acetic acid was added followed by dropwise addition of 15 ml of water over 5 minutes. After completion of the dropwise addition, the resulting mixture was gradually cooled to 30° C. over an hour and twenty minutes. During the cooling, the acetylthio derivative was precipitated from the solution. Subsequently a mixture of 16.5 ml of methanol and 15 ml of water was added dropwise over 12 minutes. After completion of the dropwise addition, the mixture was stirred at 30° C. for another hour and filtered. The collected cyrstals were washed twice each with 25 ml of an equal volume mixture of methanol and water, and dried at a reduced pressure at 70° C. Thus, 4.7951 g of dried pure spironolactone was obtained as crystals, m.p. 204.4°–206.3° C.

On the other hand, the mother liquor (filtrate) was treated by adding 125 ml of water thereto and stirring at 20° C. for an hour, followed by filtration. The collected cystals were washed twice each with 25 ml of water and dried at a reduced pressure at 70° C. Thus, 1,360 g of dried crystals which consisted essentially of 82.9% of spironolactone and 17.1% of the 7β-acetylthio derivative were obtained.

A 1.004 g portion of the second crop crystals (that are a steroid mixture of 0.017 g of the 7β-acetylthio derivative and 0.833 g of spironolactone) in 3ml of N-methyl-2- pyrrolidone were heated to 80° C. in the presence of 45 mg of p-toluenesulfonic acid monohydrate in a nitrogen atmosphere, and 0.5 ml of thioacetic acid was added. The mixture was stirred for 2 hours, then cooled to room temperature and analyzed by means of high-performance liquid chromatography.

The analysis showed that the 7β-acetylthio derivative was decreased to 0.032 g with an increase of spironolactone to 0.933 g. In addition, a slight amount of 17-hydroxy-3-oxo-17α-pregna-4,6-diene-21-carboxylic acid γ-lactone was obtained.

Similar results are obtained when the solvent, N-metnyl-2-pyrrolidone is replaced by N,N-dimethylacetamide.

EXAMPLE 2

A steroid mixture (0.503 g) consisting essentially of 0.119 g of the 7β-acetylthio derivative, 0.376 g of spironolactone and 0.008 g of 17-hydroxy-3-oxo-17α-pregna-4,6-diene-21 -carboxylic acid γ-lactone in 1.5 ml of N-methyl-2-pyrrolidone was heated to 60° C. in a nitrogen atmosphere. Then 0.3 ml of thioacetic acid was added and stirring was continued at 60° C. for 5.5 hours. The reaction mixture was cooled to room temperature and then analyzed by high-performance liquid chromatography. The analysis showed that the amount of the 7β-acetylthio derivative is decreased to 0.039 g while 0.452 g of the spironolactone was recovered. In addition, 0.004 g of 17-hydroxy-3-oxo-17α-pregna-4,6diene-21-carboxylic acid γ-lactone was obtained.

EXAMPLES 3–5

The 7β-acetylthio derivative (0.005 g) was heated in 1.5 ml of various solvents identified in Table 1 below in a nitrogen atmosphere. Then 0.3 ml of thioacetic acid was added and the reaction was continued under stirring for the time indicated in Table 1. After the reaction mixture was cooled to room temperature, it was analyzed by high-performance liquid chromatography. The results are reported in Table 1.

TABLE 1

| Example No. | Solvent | Reaction temp. (°C.) | Reaction time (hr.) | Composition of reaction product (mole %) | | |
|---|---|---|---|---|---|---|
| | | | | Spironolactone | β-Acetylthio derivative | 17-Hydroxy-3-oxo-17α-pregna-4,6-diene-21-carboxylic acid γ-lactone |
| 3* | Benzene | 75 | 2.0 | 92.3 | 7.5 | — |
| 4 | Pyridine | 60 | 6.0 | 86 | 9 | 4 |
| 5 | Methanol | 60 | 4.0 | 90 | 4 | 0.5 |

*Only in Example 3, 23 mg of p-toluene sulfonic acid monohydrate was used.

Having now fully described the invention, it will be apparent to one of ordinary skill in the art that many changes and modifications can be made thereto without departing from the spirit of the invention as set forth herein.

What is claimed as new and intended to be covered by letters patent is:

1. A method for preparing 7α-acylthio-4-en-3-oxosteroids, comprising, contacting a steroidal material which contains a 7β-acylthio-4-en-3-oxosteriod with a thiocarboxylic acid.

2. The method according to claim 1 wherein the 7β-acylthio-4en-3-oxosteroid is 7β-acetylthio-17-hydroxy-3-oxo-17α-pregn-4-ene-21-carboxylic acid γ-lactone.

3. The method according to claim 1 or 2 wherein the thiocarboxylic acid is thioacetic acid.

4. The method according to any of claims 1 to 3 wherein the steroidal material is contacted with a thiocarboxylic acid in a solvent.

5. The method according to any of claims 1 to 4 wherein the solvent is a nitrogen-containing organic compound.

6. The method according to claim 5 wherein the nitrogen-containing organic compound is selected from N-methyl-2-pyrrolidone and N,N-dimethylacetamide.

7. The method according to any of claims 1 to 6 wherein an acid having a higher acidity than the thiocarboxylic acid is present in the system.

8. The method according to any of claims 1 to 7 wherein the steroidal material is a composition which contains at least one 7β-acylthio-4-en-3-oxosteroid and at least one 4,6-dien-3-oxosteroid.

9. The method according to claim 8 wherein the 4,6-dien-3-oxosteroid is 17-hydroxy-3-oxo-17α-pregna-4,6-diene-21-carboxylic acid γ-lactone.

10. The method according to any of claims 1 to 9 wherein the 7β-acylthio-4-en-3-oxosteroid containing starting material is recovered from the residual portion of a reaction mixture which is obtained by the additional reaction of a thiocarboxylic acid to a 4,6-dien-3-oxosteroid in a solvent and from which the 7α-acylthio-4-en-3-oxosteroid product is separated.

11. The method according to claim 10 wherein the addition reaction of a thiocarboxylic acid to a 4,6-dien-3-oxosteroid is carried out either in N-methyl-2-pyrrolidone or in N,N-dimethylacetamide.

12. The method according to claim 10 or 11 wherein the separation of the 7α-acylthio-4-en-3-oxosteroid from the reaction mixture is performed by crystallization.

* * * * *